United States Patent [19]

Ellner

[11] 4,201,916
[45] May 6, 1980

[54] ULTRAVIOLET RADIATION SENSOR FOR USE IN LIQUID PURIFICATION SYSTEM

[76] Inventor: Sidney Ellner, R.F.D. #2, Bedford, N.Y. 10506

[21] Appl. No.: 888,179

[22] Filed: Mar. 20, 1978

[51] Int. Cl.² .................. G01J 1/42; G01N 21/26; G01N 21/00
[52] U.S. Cl. .................................. 250/372; 250/435; 250/455
[58] Field of Search ............. 250/338, 372, 455, 435, 250/432 R, 373, 436; 210/96 R; 422/24

[56] References Cited

U.S. PATENT DOCUMENTS

| | | | |
|---|---|---|---|
| 2,648,774 | 8/1953 | Whitlock | 250/435 |
| 3,247,413 | 4/1966 | Bisso et al. | 313/101 |
| 3,562,520 | 2/1971 | Hippen | 250/432 |
| 4,038,547 | 7/1977 | Hoesterey | 250/338 |

*Primary Examiner*—Alfred E. Smith
*Assistant Examiner*—Carolyn E. Fields
*Attorney, Agent, or Firm*—Edward F. Levy

[57] ABSTRACT

An ultraviolet radiation sensor for use in a liquid purification system senses ultraviolet radiation present in an incident beam containing ultraviolet and visible radiation and includes a beamsplitter which reflects ultraviolet radiation and transmits visible radiation. The reflected ultraviolet radiation impinges on a glass plate having a phosphor layer which emits visible radiation. The visible radiation emitted impinges on a photocell which is connected to an electrical meter and thereby provides a measure of the ultraviolet radiation present. The visible radiation transmitted through the beamsplitter enables visual monitoring of a source of radiation while simultaneous ultraviolet measurements are made.

8 Claims, 3 Drawing Figures

U.S. Patent    May, 6, 1980    4,201,916

ULTRAVIOLET RADIATION SENSOR FOR USE IN LIQUID PURIFICATION SYSTEM

The present invention relates generally to ultraviolet radiation sensing devices and more particularly to an ultraviolet radiation sensing device which incorporates an optical beamsplitter.

The prior art related to ultraviolet radiation sensing devices includes devices such as the photomultiplier tube and the ultraviolet sensitive phototube. These devices both have the disadvantage of requiring relatively high anode potentials for operation. In addition, the ultraviolet sensitive phototube is an avalanche type device which cannot record incremental changes in ultraviolet radiation. The photomultiplier tube and the ultraviolet sensitive phototube are also relatively complex and costly devices.

Efforts to overcome the disadvantages of the photomultiplier tube and the ultraviolet sensitive phototube has led to the development of the device shown in U.S. Pat. No. 3,247,413, entitled "Ultra-Violet Radiation Sensing Device", in which incident radiation, which includes ultraviolet radiation, impinges on an optical band-pass filter which transmits radiation of a selected wavelength, such as ultraviolet radiation. The radiation transmitted by the band-pass filter impinges on a phosphor layer which emits radiation in the visible range. This visible radiation is sensed by a photocell, the resistance of which varies according to the intensity of the incident visible radiation. The photocell thus provides a measure of incremental changes in the ultraviolet radiation present in the incident radiation which impinges on the optical band-pass filter.

In practice, when the aforementioned device is used for continuous measurement of ultraviolet radiation over a prolonged period, it has been found that the accuracy of the device progressively declines. This deterioration in the accuracy of the device is due to the use of the band-pass filter, which, when exposed to ultraviolet radiation on a prolonged and continuous basis, tends to solarize in the sense that it acts as its own filter, transmitting less and less ultraviolet radiation to pass therethrough. Such solarization of the band-pass filter therefore results in inaccurate readings of low ultraviolet intensity.

When such an ultraviolet radiation sensing device is used as an element in an automatic measurement and control system such as disclosed in U.S. Pat. No. 3,948,772, entitled "Split-Stream Ultraviolet Purification Device", the problem of progressive deterioration of accuracy is extremely serious. In this purification device an ultraviolet radiation sensor is used to monitor the ultraviolet radiation transmitted through a constantly flowing liquid which is subjected to continuous ultraviolet radiation as part of a purification process. If the ultraviolet radiation sensor detects a low level of radiation passing through the flowing liquid (such as would be caused by impurities in the liquid), then the purification device slows the flow of fluid in an effort to permit an additional dosage of radiation to effect proper purification. A false low reading resulting from solarization of the band-pass filter would cause an unnecessary decrease in the liquid output and therefore a deterioration of the overall efficiency of the purification device.

In accordance with the present invention there is provided an ultraviolet radiation sensing device in which an incident beam of radiation, containing both ultraviolet and visible wavelengths impinges on a beamsplitter which causes the ultraviolet radiation component of the incident beam to be deflected through an angle which is approximately 90 degrees. The deflected ultraviolet impinges on an ultraviolet sensor of a known type, which is capable of measuring small increments of ultraviolet radiation, such as the phosphor layer and photocell combination shown in U.S. Pat. No. 3,242,413. The visible light component of the incident beam of radiation passes through the beamsplitter and then continues through a viewing port which is in general alignment with the centerline of the incident beam of radiation. The viewing port may be used for viewing the source of radiation. The invention features the use of a glass plate-type beamsplitter which is made of a type of glass which is known to absorb ultraviolet radiation.

The ultraviolet radiation sensing device according to the present invention may be applied in any one of a number of applications, one of which is a liquid purification system in which a plurality of ultraviolet radiation lamps are disposed in a cylindrical tank. The ultraviolet radiation sensing device is mounted adjacent to a port on the tank which is opposite one of the plurality of ultraviolet radiation lamps. Liquid that is to be subjected to ultraviolet purification is introduced into the tank and flows past the ultraviolet radiation lamps. The ultraviolet sensor senses the amount of ultraviolet radiation which is transmitted through the liquid and thereby determines the adequacy of the ultraviolet radiation dosage. The viewing port on the ultraviolet radiation sensing device permits inspection of the ultraviolet radiation lamp thereby facilitating monitoring of the condition of the surface of the ultraviolet radiation lamp without the need to disassembly of the tank.

It is an object of the present invention to overcome the disadvantages of the prior art by providing an ultraviolet radiation sensor which eliminates the need for a selective wavelength band-pass filter.

Another object of the present invention is to provide an ultraviolet radiation sensor which incorporates a beamsplitter which separates ultraviolet radiation from visible radiation, and is not subject to deterioration caused by the solarization phenomenon which is inherent in the conventional band-pass filters.

Another object of the present invention is to provide an ultraviolet radiation sensor which permits direct viewing of the radiation source.

Still another object of the present invention is to provide an ultraviolet radiation sensor which is both rugged and economical in manufacture.

Additional objects and advantages of the invention will become apparent during the course of the following specification, when taken in connection with the accompanying drawings in which.

Figure 1:
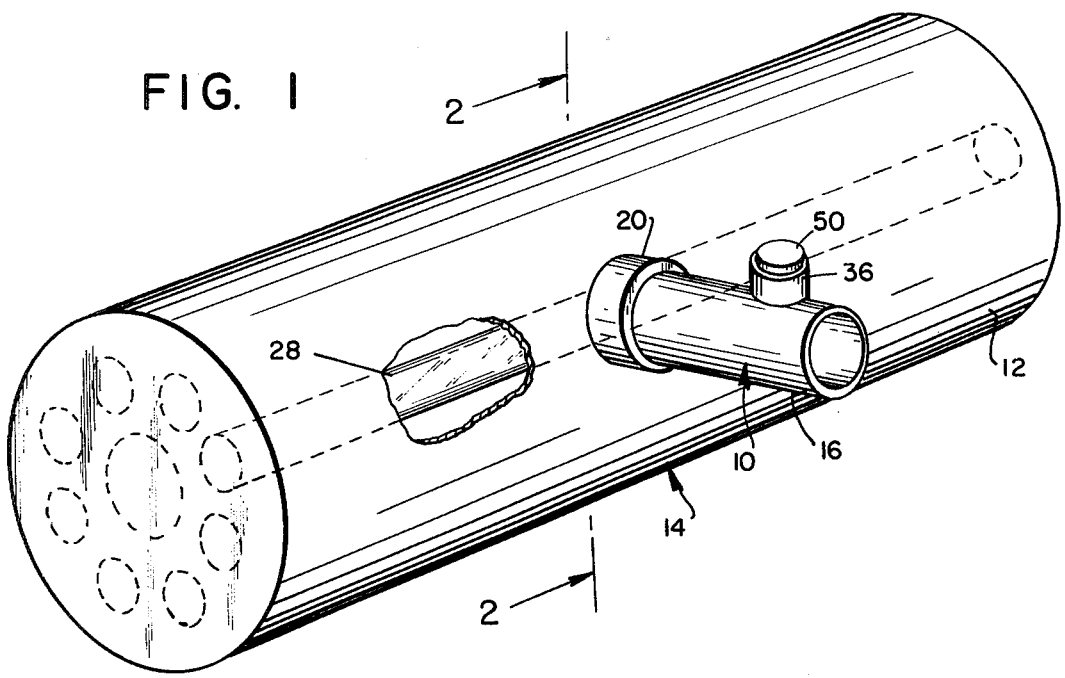
FIG. 1 is an overall perspective view of an ultraviolet radiation sensor made in accordance with the present invention and shown mounted on a liquid purification tank, with a portion of the tank shown broken away to reveal internal details, of construction.

Referring in detail to the drawings, there is shown in FIG. 1 an ultraviolet radiation sensor 10 made in accordance with the present invention and shown mounted on the wall 12 of an ultraviolet purification tank 14. The ultraviolet radiation sensor 10 comprises a support tube 16 having an inner open end 18 which is mounted on an annular flange 20 projecting radially from the wall 12 of the tank 14.

Figure 2:
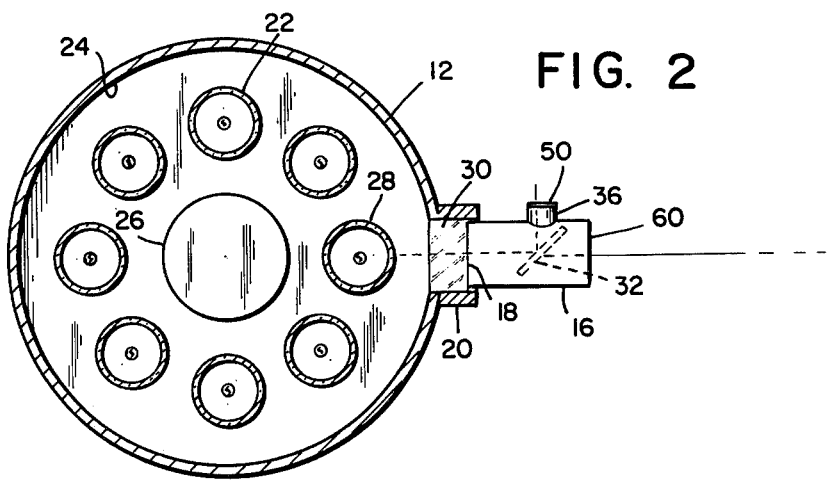
FIG. 2 is a cross-sectional view taken along the line 2—2 of FIG. 1.
Figure 3:
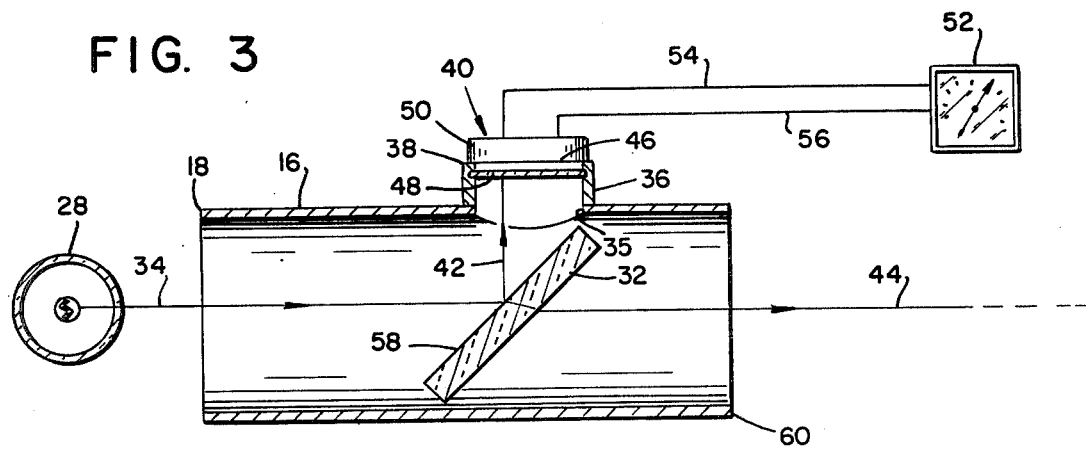
FIG. 3 is an enlarged central longitudinal sectional view of the ultraviolet radiation sensor shown in FIG. 2, showing connections to an electrical meter and showing the path of a beam of radiation from an ultraviolet radiation lamp through said sensor.

The tank 14 contains a plurality of ultraviolet lamps 22 which emit both ultraviolet and visible radiation. The lamps 22 are evenly spaced from each other and are arranged in a circular array, when viewed from an end, as is shown in FIG. 2. The radius of the centers of the lamps is such that the lamps 22 are spaced equally between the interior surface 24 of the tank 14 and the tank core 26, so that liquid in all portions of the tank 14 receives radiation of equal intensity. The flange 20, on which the support tube 16 is mounted, is located in line with the center of the lamp 28 as is shown in FIGS. 2 and 3. The flange 20 encloses a glass plate 30 which is of a type which transmits therethrough both visible and ultraviolet radiation. A suitable material for this glass plate 30 has been found to be quartz glass. The glass plate 30 and the flange 20 are sealed against leakage of liquid which is present in the tank 14 during operation of the tank 14 for the purification of liquid by exposure to ultraviolet radiation.

With reference to FIG. 3, a glass plate 32 is located at an intermediate location within the support tube 16. The glass plate 32 is disposed at a selected angle to the centerline of the incident beam 34 of combined visible and ultraviolet radiation which is generated by the ultraviolet lamp 28, and which enters the support tube through the inner open end 18. Intermediate its ends, the support tube 16 is formed with an aperture 35 bordered by a sensor mounting tube or ring 36 which projects radially from the wall thereof and communicates with the interior of the support tube 16. The upper end 38 of the sensor mounting tube 36 supports an ultraviolet radiation detector 40 which is of a conventional type.

The glass plate 32 may be made of any one of a number of glass materials which are capable of absorbing ultraviolet radiation. Quartz is unsuitable for this purpose since ultraviolet rays pass readily therethrough. On the other hand, ordinary window glass is particularly suited as the constituent material of the plate 32 since ultraviolet light is not transmitted therethrough, but is rather reflected from its surface.

It is a novel feature of the present invention that the glass plate 32 which conventionally would absorb ultraviolet radiation is disposed at a selected angle and reflects the ultraviolet component 42 of the incident beam 34 while transmitting the visible component 44 of the incident beam 34. Depending on the selected angle between the incident beam 34 and the glass plate 32 the ultraviolet component 42 of the incident beam 34 is reflected through an angle of approximately 90 degrees. Appropriate angles of incidence have been found to range between 20 degrees and 70 degrees, but for optimum results it is preferred to position the glass plate 32 at a 45 degree angle to the incident beam 34, as shown in FIG. 3.

An example of an ultraviolet detector element 40 which has been found suitable for use with the present invention comprises a phosphor layer 46 deposited on a glass plate 48 above which there is located a photocell 50. Details of construction of the phosphor layer 46 and photocell 50 combination may be found in U.S. Pat. No. 3,247,413 entitled, "Ultra-Violet Radiation Sensing Device". The photocell 50 is connected via leads 54 and 56 to an electrical meter 52 which measures the resistance of the photocell 50. Changes in the value of resistance measured by the electrical meter 52 provides a measurement of the level of ultraviolet radiation received by photocell 50 from the lamp 28, as well as an indication of any change in the level of ultraviolet radiation received by photocell 50.

The use of a glass plate beam splitting device 32 which reflects ultraviolet radiation and transmits visible radiation, thereby separating the ultraviolet from the visible radiation emitted by the ultraviolet lamps 22, eliminates the problems of the prior art in which a band-pass filter is used to separate the ultraviolet from the visible radiation. In accordance with the present invention ultraviolet radiation is reflected by the front surface 58 of the glass plate 32 beamsplitter rather than being permitted to enter the optical medium as is the case in a band-pass filter. This prevents deterioration of the accuracy of the ultraviolet radiation sensor 10 due to the effects of ultraviolet radiation energy within an optical medium.

Visible radiation 44 passes through the glass plate 32 and continues through the outer open end 60 which acts as a viewing port. The ultraviolet radiation lamp 28 may thus be viewed directly while ultraviolet radiation measurements are made simultaneously.

In an alternative embodiment of the invention, which is not shown, the support tube 16 includes a telescope, disposed at the second end 60, which permits close viewing of the ultraviolet radiation source.

Although a beam splitter 32 constituting a glass plate has been shown and described herein, other alternative beam splitting devices capable of reflecting ultraviolet radiation and transmitting visible radiation may be used.

In utilizing the invention herein, it is intended that the measurement of the level of ultraviolet radiation, which is fed as a measure of the resistance of photocell 50 through leads 54, 56 to the meter 52, is also fed to an automatic monitoring and control system which is operative to insure that the liquid flowing through tank 14 receives a sufficient dosage of ultraviolet radiation. Such monitoring and control systems are conventional and well-known, and operate, upon receiving information from the ultraviolet detector that an insufficient level of ultraviolet radiation is passing through the flowing liquid, to decrease the rate of flow of the liquid, add pure liquid thereto, or recirculate the liquid. One form of such automatic monitoring and control system is disclosed in the aforementioned U.S. Pat. No. 3,948,772, to which reference is made for further disclosure.

While a preferred embodiment of the invention has been shown and described herein, it is obvious that numerous omissions, changes and additions may be made in such embodiment without departing from the spirit and scope of the invention.

What is claimed is:

1. For use in an ultraviolet purification system in which liquid flowing through a housing is exposed to ultraviolet radiation emitted by a light source within said housing, an ultraviolet radiation sensor comprising a hollow support tube having a first open end and a second open end, and adapted to be mounted on a wall of said housing with said open end in direct communication with said light source whereby to receive an incident radiation beam from said light source, beamsplitting means disposed within said mounting tube at an intermediate location between said first end and said second end, said beamsplitting means being adapted to reflect ultraviolet radiation and transmit visible radiation and being located in line with the axis of said beam entering said support tube through said first end, ultraviolet radiation detection means mounted on said support tube in a position offset from the axis of said beam, said beam splitting means being positioned to reflect the ultraviolet radiation of said beam in a direction angular to the axis of said beam and toward said offset detection means, and to transmit the visible radiation of said beam through said support tube and out through the open second end thereof, and electrical meter means connected to said ultraviolet radiation detection means and adapted to monitor ultraviolet radiation detected by said ultraviolet radiation detection means, said ultraviolet detection means comprising a glass plate, a phosphor layer deposited on said glass plate with said phosphor layer adapted for emission of visible radiation responsive to incident ultraviolet radiation, photocell means disposed adjacent to said glass plate and adapted for receipt of said visible radiation emitted by said phosphor layer, and electrical connection means connecting said photocell and said electrical meter means.

2. An ultraviolet radiation sensor according to claim 1 in which said beamsplitting means comprises a glass plate-type beamsplitter.

3. An ultraviolet radiation sensor according to claim 2 in which said glass plate-type beamsplitter is made of ultraviolet radiation absorbing glass.

4. An ultraviolet radiation sensor according to claim 1 in which said open second end of said support tube is of sufficient size to permit visual observation therethrough of the source of said incident radiation beam, using said visible radiation trasnmitted through said beamsplitting means.

5. An ultraviolet radiation sensor according to claim 1 further including a mounting flange connected to said first end of said support tube and optical window means mounted on said mounting flange with said optical window in general alignment with said beamsplitting means, said optical window means being capable of transmitting both ultraviolet and visible radiation.

6. An ultraviolet radiation sensor according to claim 5 further including sealing means disposed on said mounting flange preventing entry of liquid into said support tube.

7. An ultraviolet radiation sensor according to claim 1 in which said beamsplitting means is disposed to reflect said ultraviolet radiation through an angle in the order of 90 degrees.

8. An ultraviolet radiation sensor according to claim 1 in which said hollow support tube has a wall aperture located intermediate said first and second ends thereof, with said ultraviolet radiation detection means mounted in communication with said aperture, said beamsplitting means comprising a glass plate mounted within said support tube in alignment with said aperture, said glass plate being disposed at an angle of approximately 45 degrees to said incident radiation beam entering said support tube, and to reflect ultraviolet radiation at an angle of approximately 90 degrees from said incident radiation beam to said aperture and said ultraviolet radiation detection means.

* * * * *